United States Patent [19]

Distenfeld et al.

[11] 4,079,628
[45] Mar. 21, 1978

[54] MIXED SPECIES RADIOIODINE AIR SAMPLING READOUT AND DOSE ASSESSMENT SYSTEM

[75] Inventors: Carl H. Distenfeld, Mattituck; Joseph R. Klemish, Jr., Bohemia, both of N.Y.

[73] Assignee: The United States of America as represented by the United States Department of Energy, Washington, D.C.

[21] Appl. No.: 763,165

[22] Filed: Jan. 27, 1977

[51] Int. Cl.² .............................................. G01N 1/22
[52] U.S. Cl. ............................ 73/421.5 R; 55/267; 55/270; 55/316; 250/304
[58] Field of Search .............. 73/28, 421.5 R; 55/316, 55/270, 267; 250/304

[56] References Cited

U.S. PATENT DOCUMENTS

| 1,501,286 | 7/1924 | Logan | 55/316 |
|---|---|---|---|
| 1,517,144 | 11/1924 | Anderson | 73/28 |
| 1,585,113 | 5/1926 | Robert | 55/316 |
| 2,744,523 | 5/1956 | Malcom, Jr. et al. | 55/316 |
| 2,939,011 | 5/1960 | Bisso et al. | 250/304 |
| 3,972,225 | 8/1976 | Fort et al. | 73/421.5 R |
| 3,983,743 | 10/1976 | Olin et al. | 55/270 |

Primary Examiner—S. Clement Swisher
Attorney, Agent, or Firm—Dean E. Carlson; Leonard Belkin

[57] ABSTRACT

This invention provides a simple, reliable, inexpensive and portable means and method for determining the thyroid dose rate of mixed airborne species of solid and gaseous radioiodine without requiring highly skilled personnel, such as health physicists or electronics technicians. To this end, this invention provides a means and method for sampling a gas from a source of a mixed species of solid and gaseous radioiodine for collection of the mixed species and readout and assessment of the emissions therefrom by cylindrically, concentrically and annularly molding the respective species around a cylindrical passage for receiving a conventional probe-type Geiger-Mueller radiation detector.

10 Claims, 3 Drawing Figures

MIXED SPECIES RADIOIODINE AIR SAMPLING READOUT AND DOSE ASSESSMENT SYSTEM

STATEMENT OF GOVERNMENT INTEREST

This invention was made during the course of, or under a contract with the Department of Civil Preparedness Agency, Department of Defense, and the United States Energy Research and Development Administration.

BACKGROUND OF THE INVENTION

In the field of atomic energy, it is desirable to provide a system for sampling gas containing a mixed species of airborne solid and gaseous radioiodine for readout and assessment of the radioemissions from the collected iodine. This is particularly advantageous for iodine containing particulates and active vapors, such as hypoiodous acid, organic iodines and aerosols created by the accidental release of solid and gaseous products from nuclear reactors and the like, when the release contains gamma ray producing $^{131}I$ and $^{135}I$, which have half-lives of about eight days and 6.7 hours respectively, since these radioisotopes of iodine and others can be absorbed and concentrated in the human thyroid gland.

One system that has been employed heretofore has separately collected the solid and gaseous species, and analyzed them with the aid of a multi-channel pulse height analyzer. However, this system, while reliable, has been difficult, complicated and expensive to operate, and has required trained personnel. Also, it has not been portable. It is further advantageous to provide a means and method for selectively and quickly determining the thyroid dose rate from airborne radioiodine with a conventional probe-type Geiger-Mueller detector, and to reduce the response of such a detection system to noble gas fission gases.

SUMMARY OF THE INVENTION

This invention provides a simple, reliable, inexpensive and portable means and method for the thyroid dose assessment of radioiodine in a gas containing a mixed species of solid and gaseous radioiodine by selectively molding the mixed species of radioiodine in a particular cylindrical, concentric, and annular arrangement for readout of the emissions by a conventional probe-type Geiger-Mueller (GM) radiation detector.

To this end, the mixed species of radioemissions producing radioiodine, which comprises a first species of airborne solid radioiodine; and a second species of airborne, gaseous organic and inorganic radioiodine are molded cylindrically, concentrically annularly by selectively collecting and encapsulating the first and second species respectively in an annular filter and an annular concentric filler that is interposed between parallel gas collimating means forming closures for the top and bottom of concentric inner and outer screens for holding the filter and filler adjacent to each other for readout and assessment of the radio emissions by a probe-type Geiger-Mueller radiation detector placed inside the inner screen.

In one embodiment, the apparatus of this invention provides a system for sampling a gas from a source of mixed solid and gaseous species of radioemissions producing radioiodine for the readout and assessment of the radioemissions by a probe-type Geiger-Mueller radiation detector for thyroid dose rate assessment purposes, the gas containing air and a mixed species of airborne radioemission producing radioiodine, comprising:

a first species of solid, elemental, particulate radioiodine with and without dust; and a second species of radioiodine hypoiodous acid vapor, radioiodine gas atoms and molecules, and organic radioiodide gas molecules; comprising:

cylindrical, concentric, inner and outer screen means forming an outer, cylindrical, longitudinally extending, first annulus having first and second parallel closure means at the top and bottom ends thereof and an inner, cylindrical, longitudinally extending passage that is concentric with the first annulus and open at one end, where it passes through one of the closure means, while being closed by one of the closure means at the other end thereof for collimating a sample of the gas containing the radioiodine for collecting the same around and in between the screen means;

cylindrical, annular filter means on the outside of the outer screen means for selectively, cylindrically and annularly molding in the shape of the filter means the first species when a sample of the gas passes through the filter means for the selective collection of the first species by the filter means;

cylindrical filler means between the screen means and adjacent to and concentric with the filter means for selectively, cylindrically, concentrically and annularly molding in the shape of the filler means the second species when a sample of the gas passes through the filler means from the filter means for the selective collection and encapsulation of the second species in the filler means, and means for causing a sample of the gas to be received and transported in between the closure means in a gas stream concentrically, annularly, inwardly and uniformly seriation by the filter and filler means so that the first and second species of airborne radioiodine in the sample are uniformly molded cylindrically, concentrically and annularly by the filter and filler means respectfully, whereby a probe-shaped Geiger-Mueller radiation detector means can be selectively inserted in one end of the passage in the inner screen means up to the other end of the passage for detecting the radioemissions that are produced between the closure means and received by the detector from the selectively molded species that are collected and encapsulated adjacent to each other in proximity to the detector as a measure of the amount of said species in the gas.

Thereupon, with the proper selection of graphic conversion means, for the detector readout, as described in more detail hereinafter, the desired sampling, collection, readout and assessment for thyroid dose rate determinations are achieved.

OBJECTS OF THE INVENTION

It is an object of this invention, therefore, to provide a means and method for sampling a gas from a source of solid and gaseous radioiodine for collection and readout and assessment of the thyroid dose rate therefrom by cylindrically, concentrically annularly molding the respective species of radioiodine around a cylindrical passage for receiving a conventional probe-type Geiger-Mueller radiation detector.

It is another object cylindrically, concentrically and annularly to mold respective species of radioiodine for separate and/or simultaneous readout and assessment by a probe-type Geiger-Mueller radiation detector.

It is a further object cylindrically, concentrically and annularly to mold respective species of radioiodine at a uniform continuous rate.

It is a still further object to provide a simple, reliable, inexpensive and portable means and method for quickly and expeditiously determining the thyroid dose rate of airborne radioiodine without requiring highly skilled personnel, such as health physicists and electronics technicians.

The above and further novel features and objects of this invention will become apparent from the following detailed description of one embodiment when read in connection with the accompanying drawing, and the novel features will be pointed out in the appended claims.

It is expressly understood, however, that the drawing is not a definition of the invention but is for purposes of illustration only.

BRIEF DESCRIPTION OF THE DRAWING

In the drawing, where like elements are referenced alike.

DESCRIPTION OF THE PREFERRED EMBODIMENT

This invention is useful in sampling a gas from a source of mixed solid and gaseous species of radioemission producing radioiodine for the readout and assessment of the emissions by a probe-type Geiger-Mueller radiation detector. More particularly, this invention is useful in providing a simple, reliable, inexpensive and portable system for quickly and expeditiously determining the thyroid dose rate of airborne radioiodine without requiring highly skilled personnel, such as health physicists and electronics technicians. To this end, a filter assembly for molding the radioiodine is mounted in a heater on a vacuum tank employing standard parts and having a simple pressure regulator for causing the required ambient air sample to flow through the filter assembly, so that a standard G.M. detector can be used with a standard calibration curve, as understood in more detail hereinafter.

Figure 2:
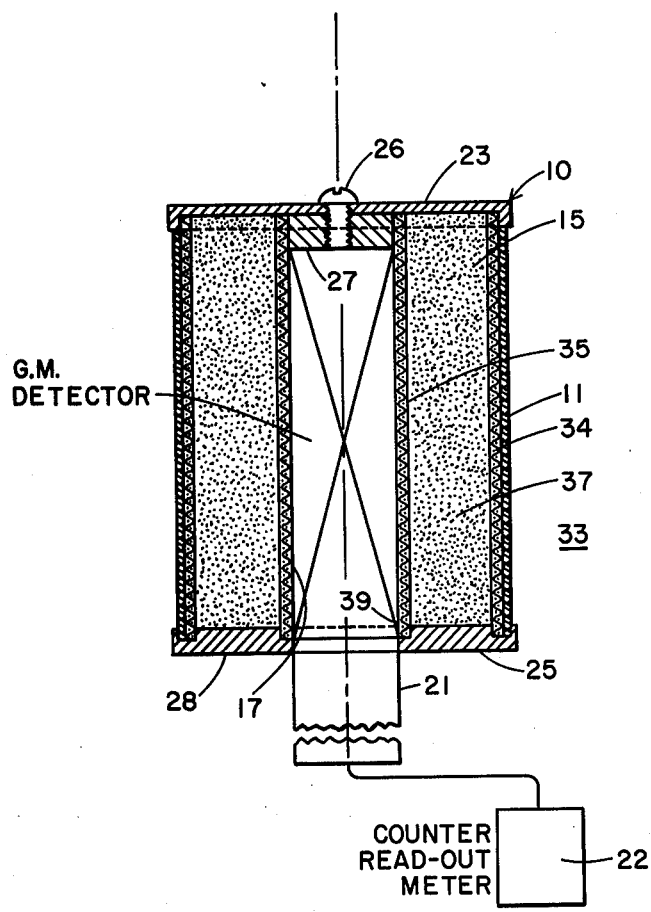
FIG. 2 is an enlarged view of the means of FIG. 1 for molding airborne, solid and gaseous radioiodine by collection and encapsulation around a cylindrical passage for receiving a conventional probe-type Geiger-Mueller radiation detector.

Referring to FIG.'s 1 and 2, the main elements of the filter assembly 10 of this invention, comprise a filter 11 for a sample gas 13 for molding the entrained solid radioiodine in an annular cylindrical configuration, and a filler 15 that is concentric with the filter for molding the entrained gaseous radioiodine around a cylindrical passage 17 for a conventional probe-type Geiger-Mueller (GM) radiation detector 21, which, as shown in FIG. 2, advantageously has a standard meter 22 detector.

Closure means 23 and 25 at the opposite ends of the filter and filler collimate a sample of the gas so that the gas flows inwardly through the filter and filler in a uniform and non-polarized stream. Also, the closure means provide means for selectively holding and renewing the filler. To this end, the closure means 23 is held by a screw 26 in plug 27, and closure 25 is glued to provide a sealing surface 28 that is selectively and removably assembled on a vacuum gas flow means 31 by contacting sealing surface 28 with sealing surface 29 of the means 31. As understood in more detail hereinafter, this means 31 has the advantage of flowing the gas 13 in a stream 32 seriation from ambient 33 through the filter and filler.

Figure 1:
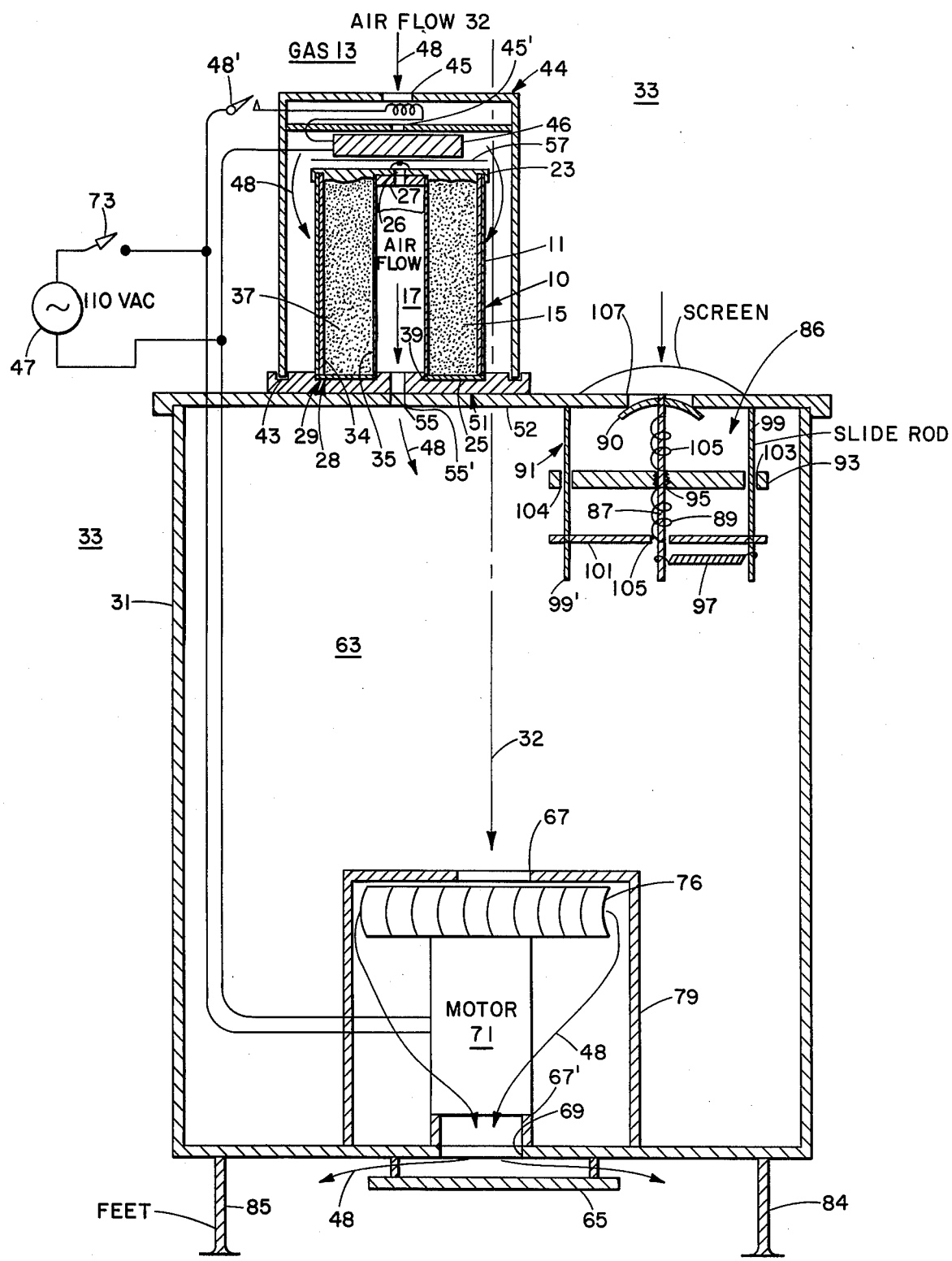
FIG. 1 is a partial cross-section of one embodiment of the apparatus of this invention.

In the practical embodiment shown in FIGS. 1 and 2, the filter and filler are held between the closure means by cylindrical, concentric, inner and outer screen means 34 and 35 forming an outer, cylindrical, longitudinally extending, first annulus 37 for the filler around passage 17. The passage 17 extends longitudinally cylindrically from the one closure means 23 through a hole 39 in the other closure means 25 for the detector 21.

As shown in the assembly of FIG. 1, a heater 44 is provided. The bottom end 43 of this heater, which is an annular cylindrical heater 44, is mounted around the assembly 10 for driving off radioactive noble gases that may be adsorbed on the filler. This reduces to a low value the detector response from these noble gases that could otherwise be molded by collection and encapsulation on the filler. The ambient air enters the heater through holes 45 and 45' in the top of the heater, and a suitable thermostatic switch 46 selectively opens and closes from a suitable electrical energy source 47 having a switch 48' to control the temperature of the heater, and thus the gas stream passing through the heater 44, which is shown by arrows 48. The gas stream is baffled as described in more detail hereinafter.

A well-shaped plate 51, which force-fits the heater and the assembly 10 on a removable top 52 on means 31, has a hole 55 that mates with a hole 55' in the top 52 for drawing a vacuum that causes the gas stream 32 to flow through the filter and filler and out through the bottom of the passage 17 in the filter assembly 10.

A top baffle 57 is located above the top closure means to cause the gas stream 32 to flow uniformly through the heater in a serpentine path toward and around the first closure means 23.

Exit baffling is also provided. To this end, the vacuum means causes the gas stream to be received from the passage 17 into vacuum chamber 63 in a first direction downwardly away from the top and bottom closure means 23 and 25 and toward baffle 65 at the bottom of the means 31. The bottom baffle 65 receives and transports the gas stream from the vacuum chamber back into the ambient air by flowing the gas along another serpentine path between openings 67, 67' and 69, so as to produce a radial annular, outward flow having a direction normal to the first downward direction. Thus, the input sample of the gas flowing into the heater and the output gas stream from the bottom baffle 65 are substantially independent of each other and there is little or no mixing of the input sample and the output gas that is derived therefrom. Bottom legs 84 and 85 support the vacuum means 31 to permit the desired exit gas flow from means 31.

The vacuum means 31 also has a pressure regulator to control the gas stream velocity and stay time. To this end, motor 71, which is selectively energized from the source 47 by switch 73, rotates the motor and its fan 76, and receives and transports the gas stream sample through holes 67, 67' and 69 in the top and bottom of motor housing 79 to cause a vacuum to be drawn while a pressure regulator 86 controls the pressure in the vacuum chamber 63. To this end, valve stem 87, which is spring loaded by spring 89, causes valve 90 in valve assembly 91 selectively to open to the ambient when the pressure decreases too much in the vacuum chamber 63, and selectively to close to seal the vacuum chamber from the ambient when the desired vacuum pressure for producing the desired stay time is achieved.

A slide bar 93 can be selectively moved up and down on threads 95 to adjust the compression of the spring 89 in valve assembly 91. A damper spring 97 keeps the valve 90 from resonating. Rods 99 and 99' hold the slide bar in relative alignment for supporting the bottom of the compression spring 89 in a stable continuously variable arrangement, and for holding the compression spring in tension against the top of plate 101. This plate 101 is rigidly connected to slider bars 99 and 99' and has a hole 105 so that the valve stem can be connected to the damper spring 97 and loaded against the side of the hole 105. The slide bar 93 and its holes 103 and 104 are free to move along the slide rods 99 and 99'. The valve 90 spans the diameter of a hole 107 to seal against the bottom of the top 52 of gas flow means 31 for providing the desired vacuum in the vacuum chamber 63. The top spring 105 merely centers the valve 90.

In the operation of the preferred embodiment shown in FIG. 1, the pressure regulator causes the gas stream to have an uniform stay time. The ambient 33 is sampled for radioiodine, although it may contain radioactive noble gases. The kinds of iodine, comprise a mixed species of first and second solid and gaseous radioiodine from a source in the general vicinity of the apparatus of this invention. Switches 73 and 48' close selectively to energize both the heater 44 and the motor 71, so that the motor fan 76 creates a vacuum in chamber 63, at a pressure controlled by pressure regulator 86. This causes the ambient air to enter the holes 45 and 45' at the top of the heater 44 and to form a uniform, non-polarized gas stream that flows in a serpentine path shown by arrows 48. The gas stream enters the center of the heater in a direction toward the top closure 23 and is deflected around that closure by baffle 57, so that the gas stream progresses outwardly toward the heater wall, radially, inwardly annularly through the filter 11 and filler 15, and downwardly through passage 17 and holes 39, 55 and 55' into the vacuum chamber 63.

The thermostat 46 maintains the temperature of the gas stream between about 110° and 130° C to drive off radioactive noble gases from the filler, while not vaporizing the radioactive iodine molded by collection and encapsulation on the filter and filler.

To catch the solid radioactive iodine, the filter 11 has heterogeneous holes formed by foraminous, matted glass-fibre paper. Since the paper has a pressure-sensitive adhesive on one surface for holding the paper against the outside of the outer screen 34, the paper can be stripped off of the outer screen 34. Thereupon, a new filter 11 is installed. Thus the radioemissions from the filter and filler can be read together or separately.

To catch the gaseous radioiodine in the sampled air, the filler is advantageously made from activated charcoal particles forming irregularly-shaped grains that will not pass through the screens 34 and 35. The grains are coated with an additive coating thereon for molding the gaseous radioiodine by collecting and encapsulating the radioactive hypoiodous acid (HOI) vapor, radioiodine gas atoms and molecules and organic redivided molecules entrained in the gas stream 32 sample.

After operating the apparatus of FIG. 1 for a predetermined length of time, the filter assembly 10 is removed from the heater and the vacuum gas flow means. Then the Geiger-Mueller detector 21 is installed in passage 17 for affecting the production of a readout and assessment of the thyroid dose rate that is read by meter 22 in accordance with the radioemissions from the radioiodine that are detected by the G.M.

Figure 3:
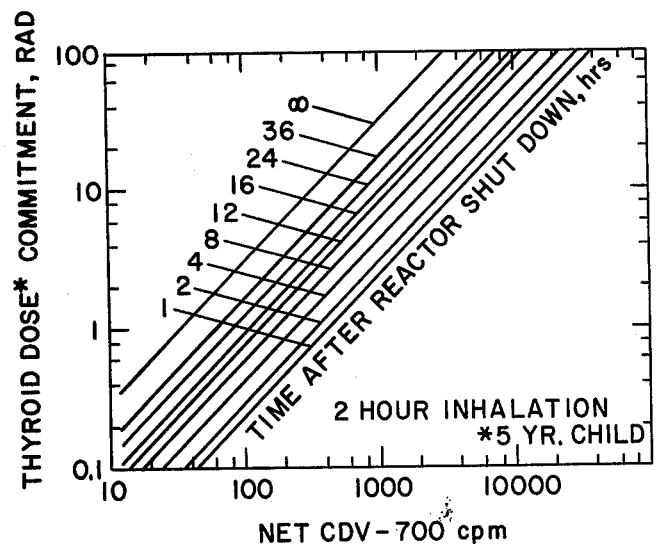
FIG. 3 is a graphic illustration of means for converting the reading from the detector of FIG. 2 into a thyroid dose rate assessment.

As shown in FIG. 3, the readout from a standard meter, such as a meter 22 that is connected to a standard G.M. detector, can be used to assess the thyroid dose rate for a wide variety of times after the source of the radioiodine releases the same into the ambient 33.

The following describes examples of the embodiment of FIG. 1:

EXAMPLE I

The filler used, which was selectively inserted and/or replaced, comprised 133g of standard 18-30 mesh, type G618 TEDA, activated charcoal grains from North American Charcoal Co. having an additive, consisting of triethylenediamine.

The filter comprised a one-sixteenth inch thick matt of glass fibre having a pressure sensitive adhesive coating applied to the outer concentric screen.

The gas stream, comprised air from the ambient containing solid, particulate radioiodine with and without dust, hypoiodous acid vapor, and gaseous radioactive atoms and inorganic and organic molecules, such as $CH_4{}^{135}I$. The flow rate was 5 cubic feet per minute with a stay time (i.e., for traversing the filter and filler) of 0.13 seconds. The ambient gas was sampled for 15 minutes before analysis.

Isotopes, comprising radioactive $^{131}I$ and $^{132}I$ and three other I isotopes were produced from a generator constructed using $< 3\mu$ thick $^{235}U$ alloy foil positioned around a $10^8$ neutron/second AmBe source. Approximately $3m^2$ of foil, containing 16.2g of $^{235}U$ was assembled on a strip $\sim$ 12 cm wide polyethylene-polypropylene open mesh and wound on a form designed to contain the neutron source. The assembly was positioned in the centroid of an aluminum pressure vessel and voids were filled with paraffin, as described in BNL report 21541, which is incorporated by reference herein. This released the desired radioiodine into the gas stream 32.

The screens, which were concentric, were perforated 0.89mm aluminum sheet having 3mm diameter 17 mesh holes constituting 35% voids compared to the area of the screens, which were 2 cm apart. The screens were glued with epoxy resin to the bottom closure, and held against the top closure by a screw through the top closure into a plug glued by epoxy resin into the detector passage. The filter assembly was a cylindrical structure measuring 7 cm in diameter $\times$ 9 cm in length with a blind hole along the axis.

By heating the incoming gas stream to between 110° and 130° C, the radioactive noble gases, such as Kr and Xe, which were otherwise collected from the air by the filler, were driven off. The thermostat was positioned in the gas stream inside the heater with a wire wrapped ceramic heater to heat the gas stream to 100° C in 1 min, and to stabilize the same to 120° C in 4–5 minutes. Heater power was removed by suitable switches after 7 minutes while the air movement continued for an additional 4 minutes to keep the collector above 95° C for $\sim$4 minutes.

The G.M. detector and meter used was a standard Civilian Defense CDV-700 system, which was used for $\sim$ 1 hour after collection.

The flow control provided by the valve assembly was up to 5% with the volume at 5 cubic feet per minute.

The gas flow means, comprised an air mover, comprising a standard 5 gal. pail having a press fitting lid and a standard vacuum cleaner motor installed therein and connected through a standard off-on switch to a standard 95-125 VAC 10 amp. source. Increases in the line voltage increased the motor speed and unregulated vacuum by a maximum of about 35%. Metal legs provided a 2.5 cm discharge air diffusion space below the pail.

Absorbed Xe removal was determined by measuring the heat induced reduction of 81 KeV $^{133}$Xe and 250 KeV $^{135}$Xe. Gamma measurements were made using a Ge (Li) detector before and after a standard heating cycle. Calibration was accomplished by slowly discharging the generator into a treated air stream that passed through the collector.

EXAMPLE II

The steps and apparatus of Example I were repeated, except that the screens were only 1.7 cm apart to reduce the thickness of the annulus therebetween and thus bring the detector closer to the filter. It was determined that the distance between the screens should be no greater than 2 cm for thyroid dose assessment using the graph of FIG. 3.

EXAMPLE III

The steps of Example II were repeated, except that the heater heated the incoming gas stream to a temperature up to 140° C. It was found that the collected iodine started to be driven off at between 130° and 140° C. At 140° C the gaseous iodine collected and encapuslated in the filter at lower temperatures was vaporized.

EXAMPLE IV

The steps of Example I were repeated, and the collection efficiency was determined to be 95% for organic and inorganic, particulate and gaseous radioiodine concentrations below stable atmospheric iodine. The heater was selectively actuated during the sampling runs to reduce the response of the detector to noble fission gases to $< 4 \times 10^{-4}$ of an equal iodine airborne activity by heating the incoming gas stream sample and the filter respectively prior to analysis to 100° C. The sensitivity of the described method and apparatus permitted a dose assessment of 1-2 rads to a child's thyroid.

This invention has the advantage of providing an easily reproduced, simple, reliable, inexpensive and portable means and method using standard parts for determining the thyroid dose rate of mixed airborne species of solid and gaseous radioiodine without requiring highly skilled personnel, such as health physicists or electronics technicians. To this end, this invention provides a sampling means and method for cylindrically, concentrically and annularly molding the respective species around a cylindrical passage for receiving a conventional Geiger-Mueller radiation detector.

What is claimed is:

1. In apparatus for sampling a gas from a source of mixed solid and gaseous species of radioemission producing radioiodine, comprising an airborne first species of solid, elemental, particulate radioiodine with and without dust; and an airborne second species of radioiodine hypoiodous acid vapor, radioiodine gas atoms and molecules and organic radioiodide molecules for the readout of the radioemissions by a probe-type Geiger-Mueller radiation detector means for thyroid dose rate assessment purposes, the improvement comprising:
  a. cylindrical, concentric inner and outer screen means forming an outer, cylindrical, longitudinally extending, first annulus having first and second parallel closure means at the top and bottom end thereof and an inner cylindrical, longitudinally extending passage that is concentric with the first annulus, and open at one end, where it passes through one of the closure means, while being closed by one of said closure means at the other end thereof for collimating a sample of the gas;
  b. cylindrical annular filter means on the outside of the outer screen means for selectively cylindrically and annularly molding in the shape of the filter means the first species when a sample of said gas passes through the filter means for the selective collection of said first species by the filter means;
  c. cylindrical filler means between the screen means and adjacent to and concentric with the filter means for selectively, cylindrically, concentrically and annularly molding in the shape of the filler means the second species when a sample of the gas passes through the filler means from the filler means for the selective collection and encapsulation of said second species in the filler means;
  d. means for causing a sample of the gas to be received and transported in between the closure means in a gas stream concentrically inwardly and uniformly seriatim by the filter and filler means so that the first and second species of airborne radioiodine in the sample are uniformly molded cylindrically, concentrically and annularly by the filter and filler means respectively, whereby a probe-shaped Geiger-Mueller radiation detector means can be selectively inserted in one end of the passage in the inner screen means up to the other end of the passage for detecting the radioemissions that are produced between the closure means and received by the detector from the selectively molded species that are collected and encapsulated adjacent to each other in proximity to the detector as a measure of the amount of said species in the gas for thyroid dose rate assessment purposes; and
  e. heater means for heating the gas stream up to at least 110° C before it passes through the filter and filler means to drive off noble gases that could otherwise be adsorbed on the filler.

2. The apparatus of claim 1 in which the cylindrical-annular filter means is a foraminous paper means formed from matted glass fibres having a pressure sensitive surface that selectively adheres to and is selectively stripible from the outside of the outer screen means.

3. The apparatus of claim 1 in which one of the closure means is removably assembled on one end of the screen means for selectively inserting and removing the filler into and from between the screen means.

4. The apparatus of claim 1 in which one end of the screen means is held by a closure means having a sealing surface that is removably assembled on and held in operable association with the means for producing the gas stream.

5. The apparatus of claim 1 in which the inner screen means has an inside diameter adapted to receive and hold a standard cylindrical probe-shaped Geiger-Mueller radiation detector means in close proximity along its length.

6. The apparatus of claim 1 in which the inner and outer screen means are spaced up to only 2 cm apart for receiving and transporting a gas stream having an air flow rate of 5 cubic feet/minute therethrough with a stay-time of .13 seconds, and the means for producing the gas stream has means for maintaining the gas stream at a constant uniform rate of flow.

7. The apparatus of claim 1 in which the filler means between the screen means is activated charcoal forming irregularly-shaped grains having an additive coating thereon for collecting radioiodine hypoiodous acid vapor, said additive coating being triethylenediamine; and the grains of charcoal have a diameter great enough to prevent the grains from passing through the screen means.

8. The apparatus of claim 1 in which the gas from the source contains noble gases, and there is provided means for controlling the temperature of the heater means for maintaining the gas stream to be below about 130° C, which is the temperature above which the collected and encapsulated iodine is driven off.

9. The apparatus of claim 1 having air regulator means for causing the gas to flow in between the closure means in a non-polarized stream, uniformly, annularly, inwardly seriatim at a substantially constant flow rate through the filter and filler for providing a substantially uniform stay time for the gas sample throughout the filter and filler means.

10. The apparatus of claim 9 having first baffle means for distributing the gas stream to flow uniformly through the heater means in a serpentive path from a first opening co-axial with the inner, cylindrical, longitudinally extending passage in a first direction toward and around the first closure means, and to flow radially, annularly, inwardly through the filter, filler and screen means toward the passage; means forming a vacuum chamber for receiving the gas stream from the passage in a direction away from the first and second closure means; and second baffle means for receiving and transporting the gas stream from the vacuum chamber into the ambient air in a serpentine path from an opening co-axial with the first opening in a radial, annular, outward, flow having a direction normal to the first direction.

* * * * *